(12) United States Patent
Cefalo et al.

(10) Patent No.: US 10,239,847 B1
(45) Date of Patent: Mar. 26, 2019

(54) METHOD FOR 2-OXOTHIAZOLIDINE-4-CARBOXYLIC ACID FOR CELLULAR GLUTATHIONE

(71) Applicant: JBP Group LLC, South Jordan, UT (US)

(72) Inventors: Dustin Cefalo, Hyrum, UT (US); Homayoun Mokri, North Logan, UT (US)

(73) Assignee: Cellactin, South Jordan, UT (US)

( * ) Notice: Subject to any disclaimer, the term of this patent is extended or adjusted under 35 U.S.C. 154(b) by 0 days.

(21) Appl. No.: 15/449,778

(22) Filed: Mar. 3, 2017

Related U.S. Application Data (60) Provisional application No. 62/303,146, filed on Mar. 3, 2016.

(51) Int. Cl.
| | | |
|---|---|---|
| *C07D 277/14* | (2006.01) | |
| *A61K 31/426* | (2006.01) | |
| *A61K 9/00* | (2006.01) | |
| *G01N 33/15* | (2006.01) | |
| *G01N 33/68* | (2006.01) | |
| *A23L 33/10* | (2016.01) | |

(52) U.S. Cl.
CPC ............ *C07D 277/14* (2013.01); *A23L 33/10* (2016.08); *A61K 9/0019* (2013.01); *A61K 9/0053* (2013.01); *A61K 31/426* (2013.01); *G01N 33/15* (2013.01); *G01N 33/6893* (2013.01); *A23V 2002/00* (2013.01); *G01N 2800/122* (2013.01); *G01N 2800/52* (2013.01)

(58) Field of Classification Search
CPC .................................................. C07D 277/14
See application file for complete search history.

(56) References Cited

U.S. PATENT DOCUMENTS

| 4,006,057 A | 2/1977 | Sano et al. |
|---|---|---|
| 4,335,210 A | 6/1982 | Meister et al. |
| 4,647,571 A | 3/1987 | Meister et al. |
| 5,095,027 A | 3/1992 | Goldberg et al. |
| 5,298,516 A | 3/1994 | Ishihara et al. |
| 5,356,918 A | 10/1994 | Ishihara et al. |
| 5,413,999 A | 5/1995 | Vacca et al. |
| 5,430,045 A | 7/1995 | Goldberg et al. |
| 5,869,679 A | 2/1999 | Verhoff et al. |
| 5,955,450 A | 9/1999 | Breborowicz et al. |
| 6,007,827 A * | 12/1999 | Galey ............... A61Q 19/02 424/401 |
| 6,177,434 B1 | 1/2001 | Kopke et al. |
| 6,369,106 B1 | 4/2002 | Atlas et al. |
| 6,685,917 B2 | 2/2004 | Rosenthal et al. |
| 7,022,317 B2 | 4/2006 | Erdelmeier et al. |
| 7,678,833 B2 | 3/2010 | Ott |
| 2002/0119104 A1 | 8/2002 | Rosenthal et al. |
| 2004/0141949 A1 | 7/2004 | Rosenthal et al. |
| 2005/0070477 A1 | 3/2005 | Cochrane |
| 2005/0129635 A1 | 6/2005 | Erdelmeier et al. |
| 2006/0128720 A1 | 6/2006 | Kufe et al. |
| 2007/0014860 A1 | 1/2007 | Rosenthal et al. |
| 2007/0014861 A1 | 1/2007 | Rosenthal et al. |
| 2007/0270350 A1 | 11/2007 | Singh |
| 2009/0053172 A1 | 2/2009 | Aquino et al. |
| 2009/0074682 A1 | 3/2009 | Lucet-Levannier |
| 2011/0245188 A1 | 10/2011 | Singh |
| 2012/0046232 A1 | 2/2012 | Kalivas et al. |
| 2012/0189602 A1 | 7/2012 | Cochrane |
| 2014/0080795 A1 | 3/2014 | Rahman |

OTHER PUBLICATIONS

Santa Cruz Biotechnology, Procysteine Safety Data Sheet, Jul. 8, 2014, pp. 1-6 (Year: 2014).*
Merriam-Webster, definition of solution, https://www.merriam-webster.com/dictionary/solution, obtained Mar. 31, 2018 (Year: 2018).*
Falb et al. J. Org. Chem. 1999, 64, 498-506 (Year: 1999).*
Falb et al. Synth. Commun. 1993, 23, 2839-2844 (Year: 1993).*
Masahiko Seki, Masanori Hatsuda, Yoshikazu Mori, Shin-Ichi Yoshida, Shin-Ichi Yamada, Toshiaki Shimizu, "A Practical Synthesis of (+)-Biotin from L-Cysteine", Chemistry—A European Journal, Oct. 29, 2004, pp. 6102-6110, vol. 10, No. 23.
M. D'Ischia, G. Prota, R.C. Rotteveel, W. Westerhof, "A Facile Synthesis of 2-Oxo-Thiazolidines of Biological Interest", Synthetic Communications, 1987, pp. 1577-1585, vol. 17, No. 13.
Eliezer Falb, Abraham Nudelman, Alfred Hassner, "A Convenient Synthesis of Chiral Oxazolidin-2-Ones and Thiazolidin-2-Ones and an Improved Preparation of Triphosgene", Synthetic Communications,1993, pp. 2839-2844, vol. 23, No. 20.
Takeo Kaneko, Takeo Shimokobe, Yoshimoto Ota, Ekido Toyokawa, Toshishige Inui, Tetsuo Shiba, "Syntheses and Properties of 2-Oxothiazolidine-4-Carboxylic Acid and its Derivatives", 1963, pp. 242-244, vol. 37, No. 2.

\* cited by examiner

*Primary Examiner* — Matthew P Coughlin
(74) *Attorney, Agent, or Firm* — Kunzler, PC (57) ABSTRACT

Provided herein is a composition, method of manufacture, and method for treating a disease condition and/or raising cellular levels of glutathione, the composition comprising L-2-oxothiazolidine-4-carboxylate, (procysteine) having a purity of at least 99 to 99.5 percent.

8 Claims, 8 Drawing Sheets

SPECIFICATION/CERTIFICATION DOCUMENT

Product Name   Cystox™
Chemical Name  R-2-Oxothiazolidine-4-Carboxylic Acid
Common Name    Procysteine Product Code L-15371
CAS # 19771-63-2
Molecular Weight 147.15
Formula $C_4H_4O_3NS$

| Test | Specification | Result | Method |
|---|---|---|---|
| Appearance | White to Off White | | Visual |
| Form | Powder | | Visual |
| Odor | Sulfur | | Organoleptic |
| Solubility Color | Colorless to Slight Yellow | | 1% Solution @ 20°C |
| pH (1% Solution @ 20° C) | 2.0 - 2.5 | | pH Meter |
| Purity | ≥ 99% | | HPLC |
| Purity | ≥ 99% | | Titration |
| NMR | Conform to Structure | | Proton and Carbon |
| Specific Rotation | -61 to -66 Deg (C=1, H2O) | | Polarimetry |
| Lead | <5 mcg/1.5 g | | ICP-MS |
| Arsenic (Inorganic) | <2 mcg/1.5 g | | ICP-MS |
| Cadmium | <1 mcg/1.5 g | | ICP-MS |
| Mercury (Total) | <0.5 mcg/1.5 g | | CVAA |
| Total Plate Count | <1,000 cfu/g | | AOAC 990.12 |
| E. Coli | <10 cfu/g | | AOAC 990.12 |
| Yeast and Mold | <100 cfu/g | | AOAC 997.02 |

Batch Lot Number:
Signed By:

Verified By:

FIG. 10

METHOD FOR 2-OXOTHIAZOLIDINE-4-CARBOXYLIC ACID FOR CELLULAR GLUTATHIONE

CROSS-REFERENCES TO RELATED APPLICATIONS

This application claims the benefit of U.S. Provisional Patent Application No. 62/303,146 entitled "Method for 2-Oxothiazolidine-4-Carboxylic Acid for Cellular Glutathione" and filed on Mar. 3, 2016, for Dustin Cefalo and Homayoun Mokri, which is incorporated herein by reference.

FIELD OF THE INVENTION

This invention relates to a method for 2-oxothiazolinide-4-carboxylic acid (procysteine), the resulting high purity product, and its use for increasing cellular glutathione and treating disease.

BACKGROUND

Description of the Related Art

L-2-oxothiazolidine-4-carboxylate, also known as procysteine, is a white to off white, soluble, stable, crystalline powder with a characteristic sulfur odor. It is a cyclic derivative compound of the amino acid L-cysteine. Through the synthesis process, the free sulfur group (SH) becomes a member of the ring structure providing beneficial added oxidative stability to the sulfur. Furthermore, this moiety possesses an asymmetric carbon yielding an optically active substance. Procysteine is an intracellular precursor to cysteine in that it can be enzymatically converted to cysteine. Cysteine is the rate limiting substance in the synthesis of glutathione. Cellular levels of glutathione can be important in a number of health contexts.

For example, Acute Respiratory Disorder Syndrome (ARDS), a disorder characterized by severe lung dysfunction, is a devastating complication of conditions associated with massive acute inflammation, such as severe infection, multiple trauma and extensive burns. This disorder affects an estimated 150,000 patients in the United States annually, and has a mortality rate of approximately 40 percent. There are currently no commercially available drug treatments for ARDS. Treatment for patients suffering from ARDS is administered in a hospital intensive care unit and is generally limited to supportive care consisting of highly invasive mechanical ventilation. Mechanical ventilation involves forcing air containing high concentrations of oxygen into the lungs via an endotracheal tube inserted through a patient's nose or mouth. Due to the invasive nature of this procedure, mechanical ventilation places a patient at an increased risk of serious complications, including hospital-acquired infection with drug resistant organisms.

Multiple Organ Disfunction Syndrome (MODS), generally has catastrophic consequences for the patient. Organ systems that are frequently involved in MODS include the lungs (ARDS), the kidneys (acute renal failure), the liver (acute hepatic failure) and the heart (cardiovascular collapse). The mortality rate for MODS patients is approximately 60 percent when two organs fail and exceeds 90 percent when a third organ fails. According to some estimates over 750,000 patients annually in the United States at risk of MODS.

Current methods of manufacturing procysteine, however, are cumbersome and slow, not high yield, and typically result a maximum purity of 98 percent or less, allowing for the presence of toxic impurities with potentially deleterious side effects. Therefore, a need exists for a faster, more efficient, high yield method that produces a high purity product.

SUMMARY

From the foregoing discussion, it should be apparent that a need exists for a readily available, high purity procysteine, for a method for a high purity procysteine and for a method of treatment using high purity procysteine. Beneficially, such a method would be efficient, clean, and economical and yield a highly pure composition suitable for treating disease conditions and for increasing cellular glutathione.

The present invention has been developed in response to the present state of the art, and in particular, in response to the problems and needs in the art that have not yet been fully solved by currently available methods and procysteine compositions. Accordingly, the present invention has been developed to provide methods and a composition that overcome many or all of the above-discussed shortcomings in the art.

References throughout this specification to features or similar language do not imply that all of the features that may be realized with the present invention should be or are in any single embodiment of the invention. Rather, language referring to the features is understood to mean that a specific feature or characteristic described in connection with an embodiment is included in at least one embodiment of the present invention. Thus, discussion of the features and characteristics, and similar language throughout this specification may, but does not necessarily, refer to the same embodiment.

Furthermore, the described features, and characteristics of the invention may be combined in any suitable manner in one or more embodiments. One skilled in the relevant art will recognize that the invention can be practiced without one or more of the specific features or characteristics of a particular embodiment. In other instances, additional features and characteristics may be recognized in certain embodiments that may not be present in all embodiments of the invention.

These features and characteristics of the present invention will become more fully apparent from the following description and appended claims, or may be learned by the practice of the invention as set forth hereinafter.

Provided herein is an embodiment of a method for procysteine, the method comprising: reacting L-cysteine with triphosgene dissolved in toluene, testing the reaction for completeness; continuing the reaction to completeness if incomplete, cooling the solution to a temperature in the range of about 0-30 degrees C., concentrating and drying the product, isolating and washing the product, drying the product, testing the product for purity, and rewashing until the product reaches a purity in a range of from about 95 percent to about 100 percent. The purity is sometimes at least 99 percent.

In some embodiments L-cysteine is dissolved in a solution of water and NaOH and then mixed with the triphosgene dissolved in toluene. The solution of triphosgene dissolved in toluene may be mixed with the solution of water and NaOH slowly to form a two phase mixture while maintaining the temperature in a range of from about about 0 degrees C. to about 30 degrees C. The two phase mixture is sometimes allowed to reach a temperature in range of from about 15 degrees C. to about 55 degrees C. after the solution of triposgene has been added. In certain embodiments the temperature is in a range of from about 25 degrees to about 30 degrees C. The pH may be adjusted to a range of from about 1.0 to about 3.5 with HCL or NaOH. The pH is sometimes adjusted to 1.5.

Also provided herein is composition according to the disclosed method for treating a disease condition and/or raising blood levels of glutathione, the composition comprising procysteine having a purity in the range of from about 98 percent to about 100 percent.

Further provided herein is a method for treating a subject having a disease condition, the method comprising administering a composition of purified procysteine to the subject. The procysteine may be in a range of 98 percent to 100 percent purity. In various embodiments the subject is a mammal and may be a human being. The disease condition is sometimes acute respiratory disorder syndrome, organ disfunction, multiple organ disfunction, motor neuron degeneration, amyotrophic lateral sclerosis (ALS), cognitive impairment, Alzheimer's, Disease, immune and neuroinflammatory disease, Autism, Cardiovascular Disease, vascular system complications, Diabetes, pulmonary disorders, chronic obstructive pulmonary disorder (COPD), heavy metal-induced toxicity and carcinogenicity (including from mercury), HIV, immune deficiency virus, Macular Degeneration, retinal epithelial damage, Multiple Sclerosis, brain dopamine loss, Parkinson's Disease, Stroke, or a disease condition associated with oxidative stress.

The purified procysteine may be administered orally, through the skin, mucosa, nose, eye, parenterally, subcutaneously, intramuscularly, or intravenously. In certain embodiments the formulation is a liquid, cream, lotion, oil, emulsion, gel, paste, powder, liquid, powder aerosol (lyophilized), or sustained release formulation. In various embodiments the method further comprises evaluating the subject's symptomatic response and adjusting the dose accordingly.

Additionally provided herein is a method for increasing cellular glutathione levels in a subject by administering purified procysteine to the subject. The procysteine is sometimes in the range of from about 98 percent to about 100 purity. In some embodiments the purified procysteine is administered orally, through the skin, mucosa, nose, eye, parenterally, subcutaneously, intramuscularly, intravenously, or formulated for sustained release. The formulation may be a liquid, cream, lotion, oil, emulsion, gel, paste, powder, liquid or powder aerosol (lyophilized). In certain embodiments the method further comprises measuring the subject's blood glutathione levels and adjusting the dosage accordingly.

BRIEF DESCRIPTION OF THE DRAWINGS

In order that the advantages of the invention will be readily understood, a more particular description of the invention briefly described above will be rendered by reference to specific embodiments that are illustrated in the appended drawings. Understanding that these drawings depict only typical embodiments of the invention and are not therefore to be considered to be limiting of its scope, the invention will be described and explained with additional specificity and detail through the use of the accompanying drawings, in which.

DETAILED DESCRIPTION

Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

Furthermore, the described features, structures, or characteristics of the invention may be combined in any suitable manner in one or more embodiments. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

The schematic flow chart diagrams included herein are generally set forth as logical flow chart diagrams. As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

Figure 1:
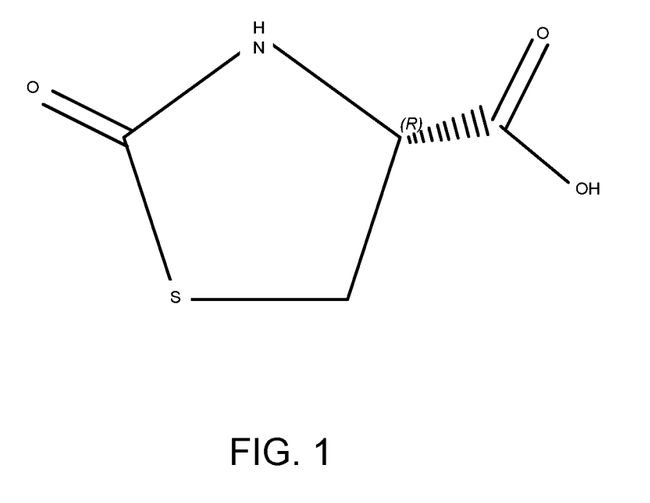
FIG. 1 is a molecular diagram depicting the procysteine molecule.

FIG. 1 is a molecular diagram depicting the procysteine molecule in accordance with the present invention. An embodiment of procysteine(L) manufactured according to the method herein has been named Cellactin. Cellactin lacks the toxic effects of cysteine and can be safely administered as a therapeutic. In the body Cellactin is converted to cysteine which is an important reactant in the formation of glutathione. Cellactin has been effective to prevent or limit oxidative tissue damage from reactive oxygen species ("ROS"), highly reactive toxic molecules produced as part of the body's immune response.

According to a carbon, hydrogen, nitrogen test (CHN) Analysis Procysteine contains:

| | | |
|---|---|---|
| Carbon % | Measured 32.55% | Theoretical 32.65% |
| Hydrogen % | Measured 3.47% | Theoretical 3.42% |
| Nitrogen % | Measured 9.51% | Theoretical 9.52% |

Figure 2:
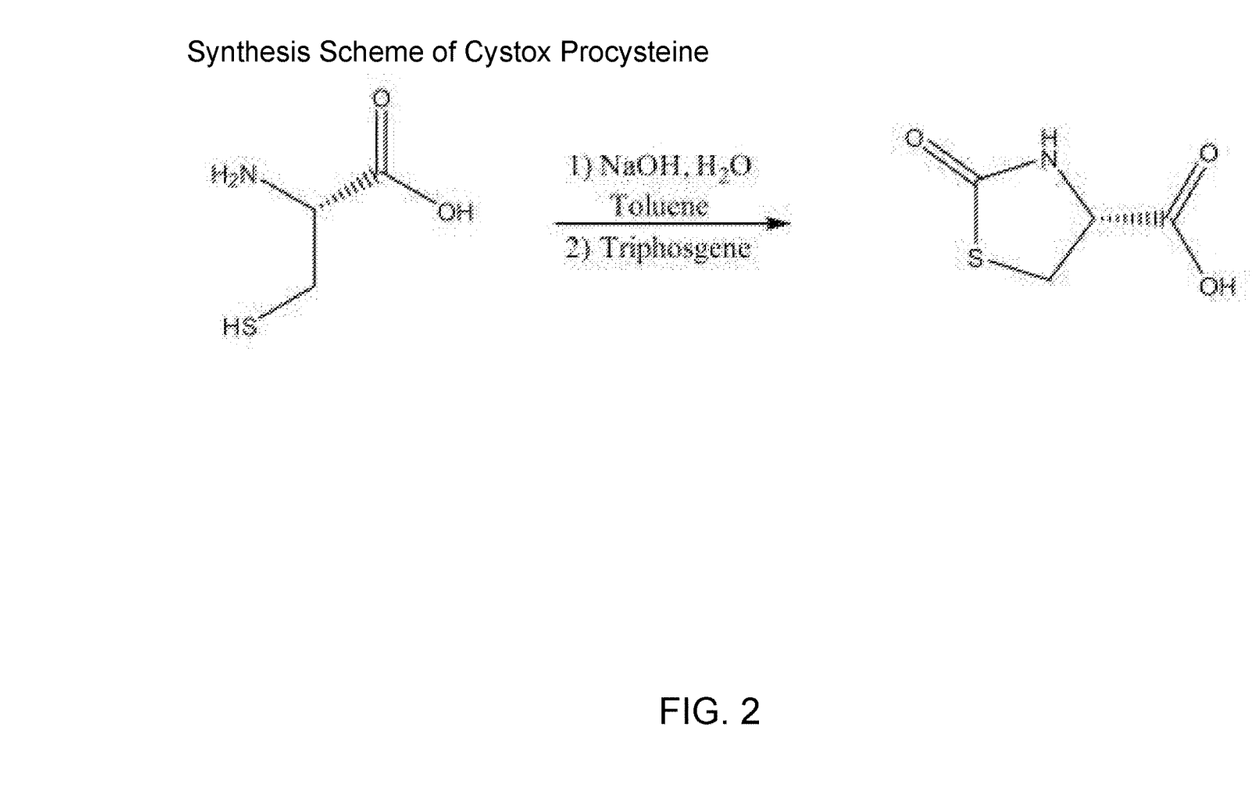
FIG. 2 is a molecular diagram depicting an embodiment of a reaction of Cysteine with triphosgene dissolved in toluene to form procysteine.

FIG. 2 is a molecular diagram depicting an embodiment of a reaction of cysteine with triphosgene dissolved in toluene to form procysteine. As depicted, when reacted with triphosgene in the presence of toluene procysteine loses one hydrogen molecule from each of nitrogen and sulphur and adds an oxygen molecule to form the procysteine ring structure thus protecting both the thiol group and the amine. Amines are nucleophilic and basic in nature and therefore can require protection to mask these properties during a chemical reaction. In the case of amine protection, after the amine sensitive reaction is complete and the protecting group removed, the amine is regenerated as it was prior to adding the protecting group.

Figure 3:
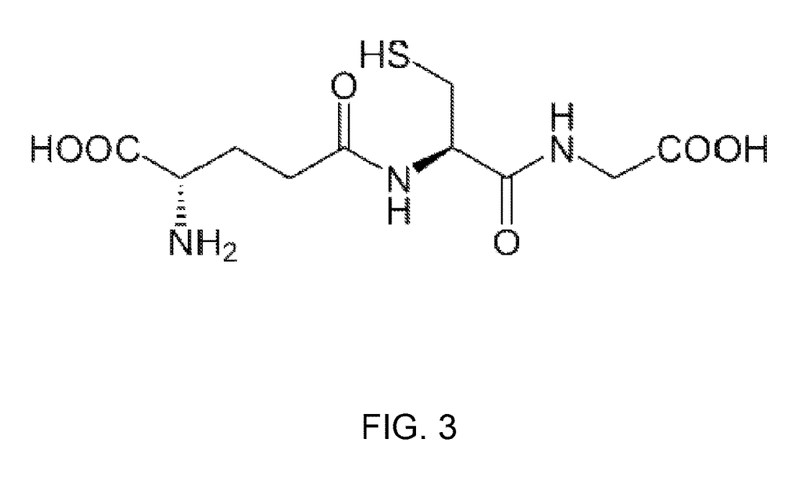
FIG. 3 is a molecular diagram depicting a glutathione molecule.

FIG. 3 is a molecular diagram depicting glutathione. Glutathione, a molecule found in high concentrations throughout the body, is one of the principal mechanisms for neutralizing reactive oxygen species (ROS). Preclinical and clinical studies have demonstrated that in some conditions involving massive acute inflammation, including severe infection, multiple trauma and extensive burns, large quantities of ROS may be produced. Studies have also indicated decreased levels of glutathione in such conditions. When the body's production of ROS increases and exceeds the capacity of glutathione and other antioxidant systems to combat oxidative stress, tissue damage in the body's major organs can result, leading to organ dysfunction and, in many cases, death.

Figure 4:
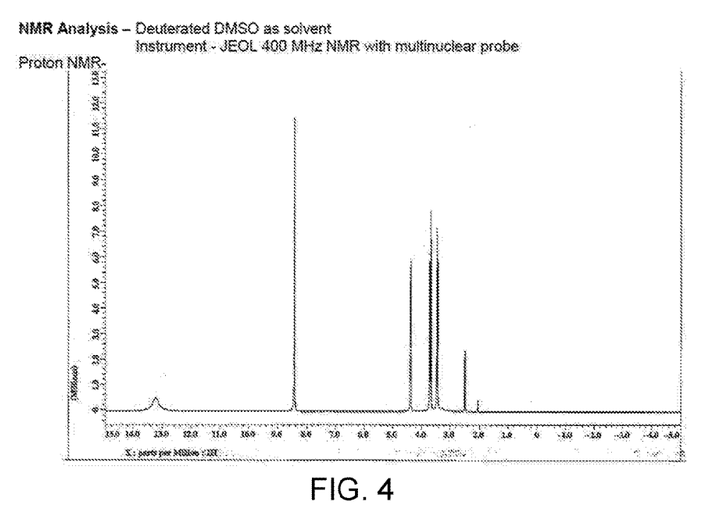
FIG. 4 is a proton Nuclear Magnetic Resonance (NMR) analysis reading depicting peaks for the component molecules of procysteine.

FIG. 4 is a proton Nuclear Magnetic Resonance (NMR) analysis reading depicting peaks for the component molecules of procysteine. In general the NMR indicates the chemical environment of hydrogen atoms, the number of hydrogen atoms in each environment and the structure of groups adjacent to each hydrogen atom. Peaks for the NMR & (DMSO, 400 mHz) are as follows reading the graph from left to right: 3.44 (dd, 1H, SCHH), 3.72 (dd, 1H NcHCO$_2$H), 4.39 (dd, 1H NCHCO$_2$H), 8.45 (s, 1H, NH), 13.25 (brs, 1H, CO$_2$H).

Figure 5:
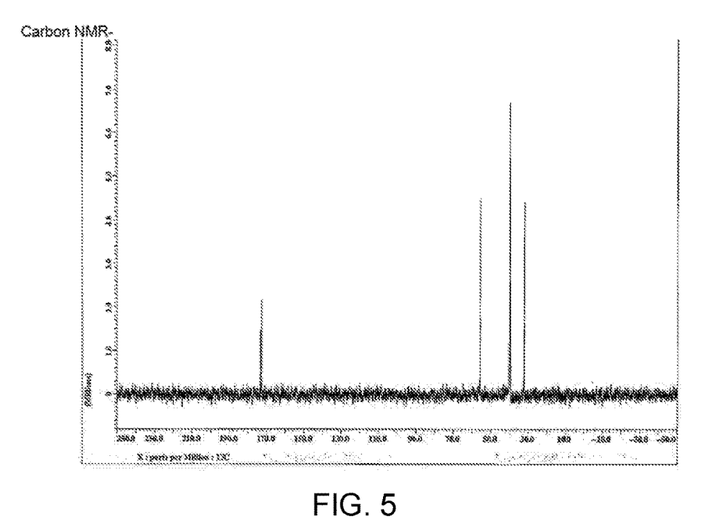
FIG. 5 is a carbon NMR analysis reading depicting peaks for the component molecules of procysteine.

FIG. 5 is a carbon NMR analysis reading depicting peaks for the component molecules of procysteine. In general the NMR indicates the chemical environment of carbon atoms, the number of carbon atoms in each environment and the structure of groups adjacent to each carbon atom. Peaks for the NMR & DMSO, 100 mHz are as follows reading the graph from left to right: 32.36 (SCH$_2$CH), 55.95 (CH$_2$CHN), 173.05 (NCOS), 173.68 (CO$_2$H).

Figure 6:
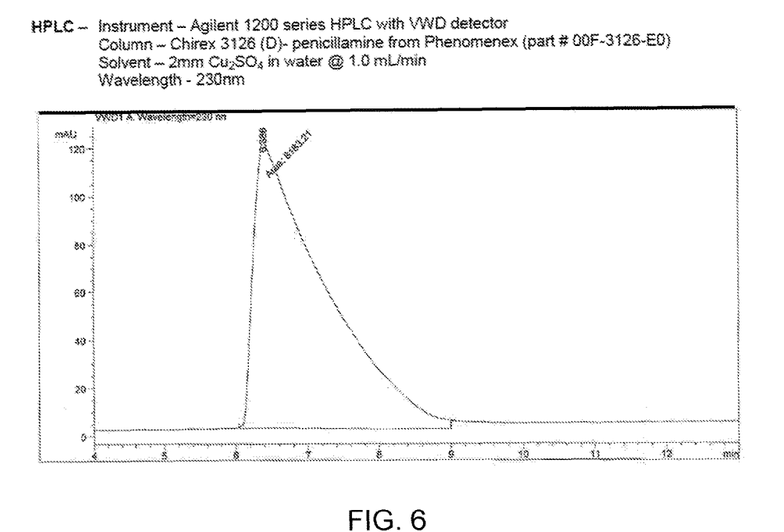
FIG. 6 is a High Performance Liquid Chromatography (HPLC) reading reading depicting an effluent curve for L procysteine.

FIG. 6 is a High Performance Liquid Chromatography (HPLC) reading reading showing the effluent curve for L procysteine. Experimental parameters were: HPLC—Instrument—Agilent 1200 series HPLC with VWD detector, Column—Chirex 3126 (D)-penicillamine from Phenomenex (part #00F-3126-E0), Solvent—2 mm Cu2SO4 in water @ 1.0 mL/min, Wavelength—230 nm.

Figure 7:
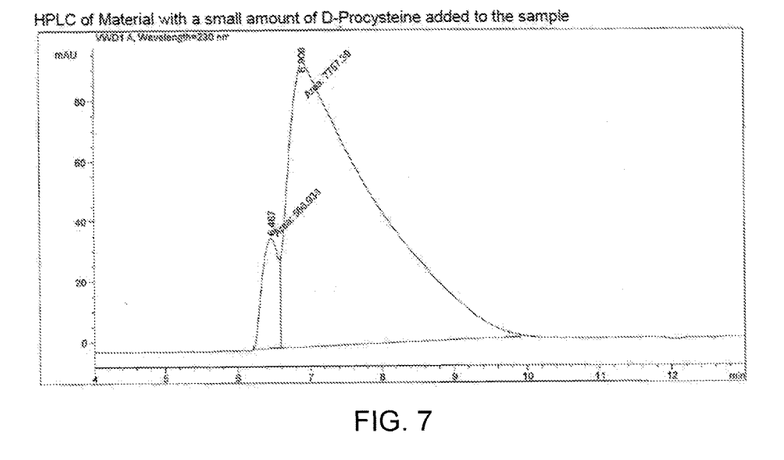
FIG. 7 is a HPLC reading depicting an effluent curve for L procysteine with small amount of D procysteine added.

FIG. 7 is a HPLC reading depicting the effluent curve for L procysteine with a small amount of D procysteine added.

The literature melting point for L procysteine was 171 C to 173 C and the observed melting point was 171 C to 173 C.

Figure 8:
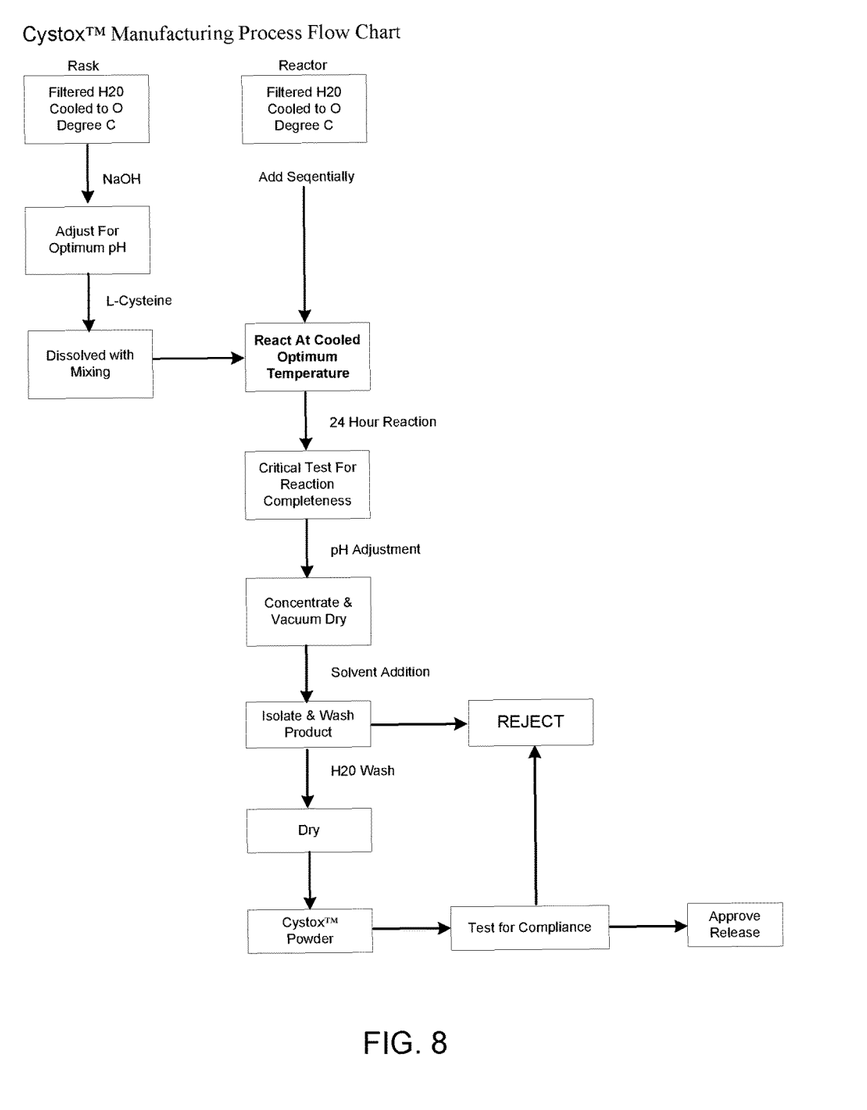
FIG. 8 depicts an embodiment of a synthesis method for the manufacture of 2-Oxo thiazolodine 4 carboxylic acid.

FIG. 8 depicts an embodiment of a synthesis method for 2-Oxo thiazolodine 4 carboxylic acid in accordance with the present invention. In certain embodiments objectives of the method included: (1) a final compound greater than 99% purity, (2) high ingredient conversion and product recovery, (3) easily available raw materials, (4) easy product isolation, and (5) reproducible method/product. In some embodiments as depicted a flask of filtered H2O was cooled to 0 degrees C. NAOH was added and the solution adjusted for pH. L-Cysteine was added and dissolved by mixing. Triphosgene was dissolved in Toluene and added to the solution and allowed to react for 24 hours at a cooled optimum temperature. In certain embodiments the reaction was then tested for completeness and adjusted for pH. The resulting solution was concentrated and vacuum dried. In various embodiments a solvent was added to the dissolved solids and the resulting solution was washed with H$_2$O and dried. The resulting powder was be tested for purity and either released for use or rewashed as indicated.

Many of the published procedures for procysteine synthesis utilize Phenyl chloroformate as a reagent, which creates phenol as a byproduct. Phenol is a toxic material and has very significant health effects if ingested, which would necessitate significant processing to ensure removal of the byproduct. Although existing methods go through extensive steps to remove this toxic material samples tested from other sources included phenol as an impurity in the product.

Other methods utilize 1,1'-Carbonyldiimidazole as a reagent, producing a byproduct of imidazole which is also significantly toxic, requiring significant processing is needed to ensure that this hazardous reagent does not persist in the final product. Low yield is a further disadvantage. Eighty four percent of the weight in the carbonyldiimidazole becomes waste, with only 16% of the molecule is included in the final product. This means that 84 percent of an expensive reagent ends up as hazardous waste.

A number of other reactions utilize lead, selenium, mercury, or other heavy metal reagents all of which are toxic when ingested. The Cellactin procysteine is formulated as a human dietary ingredient so at least 99 to 99.5 percent purity is paramount. Heavy metals, unreacted ingredients (including cysteine), or solvents must not be present in the final product. The single step compound conversion and bilayer system are two keys to ensuring a highly pure compound and maximizing the yield. Specifically, the bilayer system enables the conversion, separation, and isolation of procysteine in one layer while the undesirable materials remain in solution in the other.

Furthermore, published procedures using triphosgene with dioxane and water as a solvent report a yield of only 77 percent while the process provided herein yields 90-95 percent. The ability to realize 13-18 percent more final product from the same amount of reagent may substantially decrease the cost of the product, especially when produced on very large scale.

Any toxic reagents used as provided herein are readily and reliably removable to even below the detection the limit and/or can be easily neutralized to non-toxic compounds that are also readily removed without significant additional processing. The easy of removal of potential toxins may substantially reduce the costs and give an economically favorable process. Optimum reaction conditions such as temperature, pH, and time influence the purification and yield. The combination of reagents and reaction conditions provided herein produces unexpectedly positive results in terms of purity and yield.

Figure 9:
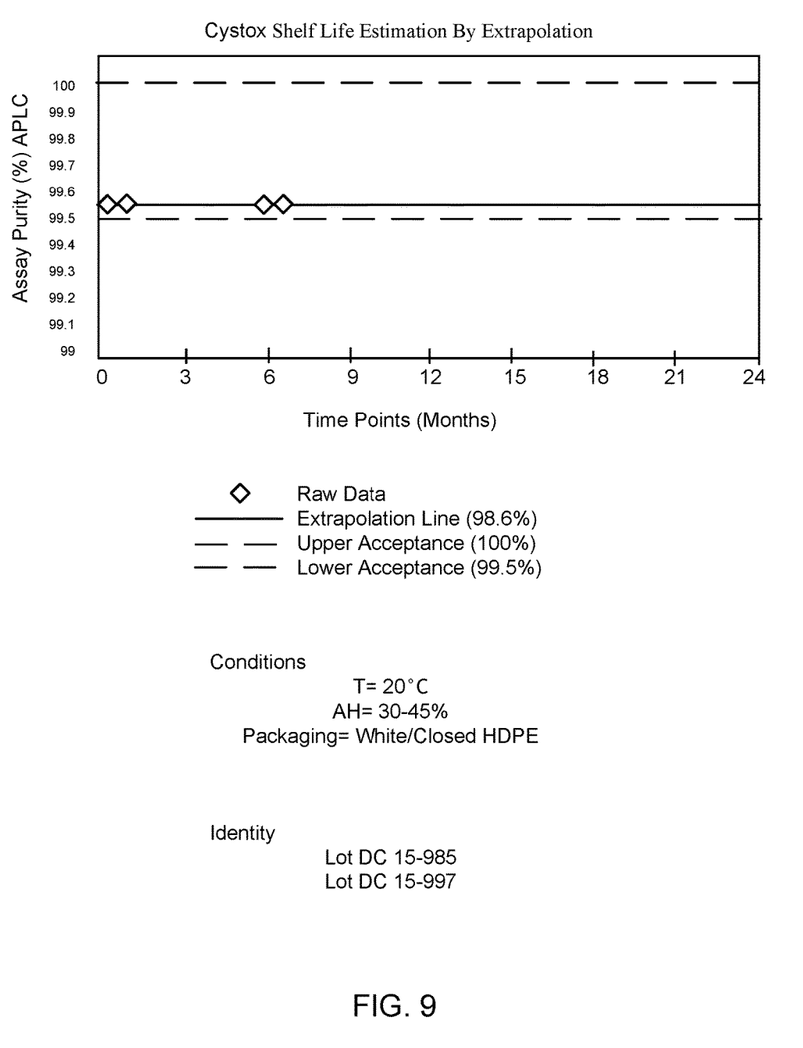
FIG. 9 depicts Cellactin shelf life estimation by extrapolation.

FIG. 9 illustrates Cellactin shelf life estimation by extrapolation. As depicted that upper dotted line indicates an upper acceptance of 100 percent stability. The lower dotted line indicates 99 percent stability. The solid line represents the extrapolation line with the triangles representing raw data. The product has been extrapolated to be stable for 2 years as supplied if stored in original package at ambient temperature and protected from heat and moisture. No purity percent change was noted for two separate Cellactin preparation batches from $T_0$ to $T_6$ (months). Confirmation of extrapolation assumes the change pattern may continue to fit model for at least 24 months.

Figure 10:
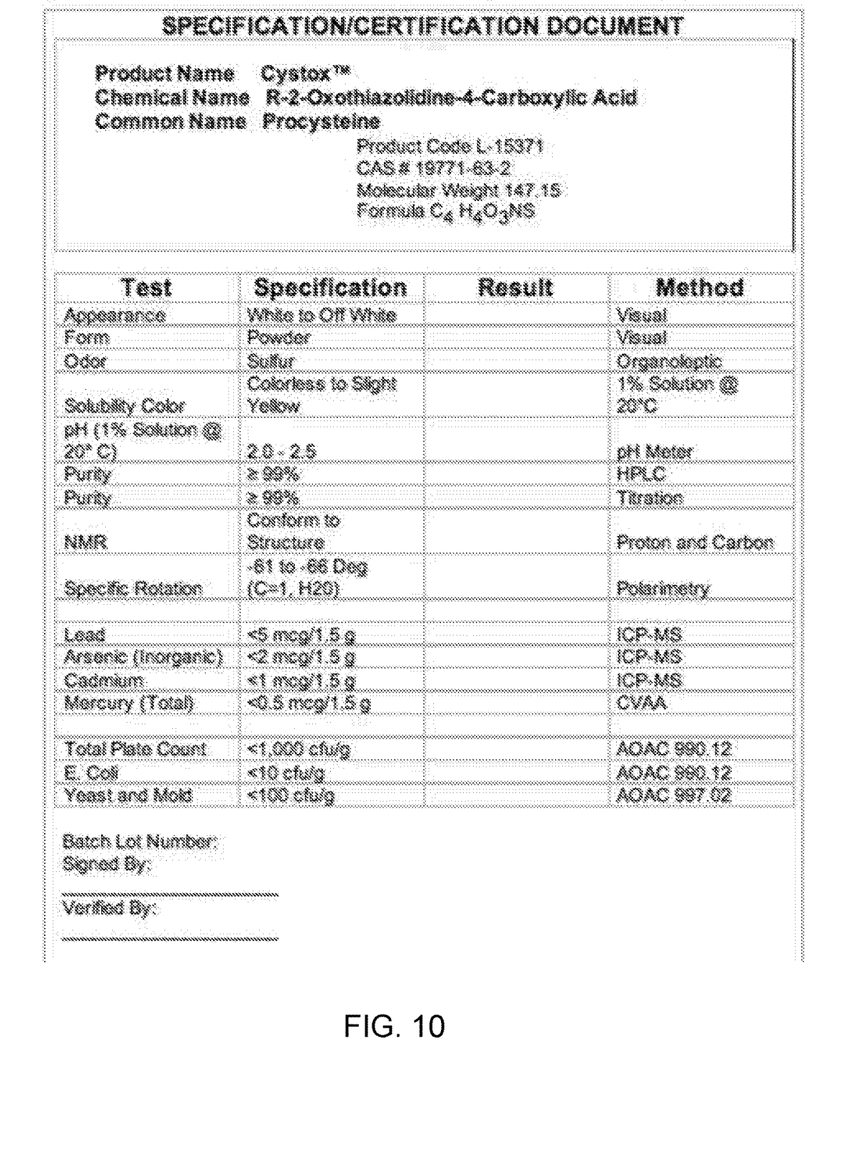
FIG. 10 shows a specification/certification document for Cystox (now Cellactin).

FIG. 10 shows a specification/certification document for Cellactin (formerly Systox).

Administration and Dosage

Examples of administration and dose may be characterized by the safety profile and pharmacokinetics of these formulations in clinical trials involving over 265 subjects in total. In general, the highest dose tested has been tolerated under the conditions of each study without adverse effects observed. Also, most previous animal studies have been conducted using intravenous (IV) administration, whereas in some embodiments procysteine (Cellactin) supplementation is oral. In human results for oral administration have been obtained for oral administration the highest dose tested has been generally well tolerated without observed adverse effects.

Utilizing animal (dog and rat) data and comparing that to the recommended daily procysteine (Cellactin) intake of 1.75 g or ~25 mg/kg, that represents 18× to 96× safety margin compared to acute no adverse effect level (NOAEL) and repeat NOAEL intravenous administration in dogs (450 mg/kg) and rats (2400 mg/kg), respectively. The safety margin may be even greater if compared to animal oral administration data.

Comparing the recommended oral, daily procysteine (Cellactin) intake of 1.75 g to that of the 9 grams per day taken for 2 years without clinically significant changes in serum chemistry or hematology, there would by a 5× safety margin, whereas it is possible that the safety margin when comparing to an adverse effect level would be considerably larger than 5×. Without knowing the NOAEL or lowest observed adverse effects level (LOAEL) for humans and based on the report of 9 grams per day taken orally for 2 years without clinically significant changes in serum chemistry or hematology, an acceptable daily intake (ADI) of up to 9 grams per day should be considered acceptable. Without knowing the NOAEL or LOAEL for humans and based on the report of 9 grams per day taken orally for 2 years without clinically significant changes in serum chemistry or hematology, the estimated daily intake (EDI) and ADI both should be considered as <9 grams/day. This would then result in an EDI/ADI ratio of 9 grams/day/9 grams/day=1. Without knowing the NOAEL or LOAEL for humans it is difficult to determine a true estimate of margin of safety. However, based on the report of 9 grams per day (129 mg/kg/day) taken orally for 2 years without clinically significant changes in serum chemistry or hematology and comparing that to the recommended oral, daily Procysteine (Cellactin) intake of 1.75 g (25 mg/kg/day) an estimate would result in 5×. However, it would be reasonable to assume that a much higher estimate of safety margin would be expected based on the 4-8× estimate comparing oral, daily Procysteine (Cellactin) intake of 1.75 grams to human intravenous NOAEL calculations shown above in section 4.1 and 18 or 96× comparing to dog and rat intravenous NOAEL calculations, respectively shown above in Section 4.1. It is reasonable to conclude that the safety margin would be even greater if compared to animal oral administration data.

Acute NOAEL and repeat NOAEL for intravenous administration in dogs was 450 mg/kg and in rats was 2400 mg/kg, with these values representing the highest dosages intravenously tested and it is assumed that the NOAEL levels would be even higher for oral administration in animals. In the human clinical trials previously conducted, procysteine (Cellactin) was well tolerated by patients, including a group that took up to 9 grams per day orally for two years without clinically significant changes in serum chemistry or hematology. Therefore, it is reasonable to expect that a recommended human oral, daily procysteine (Cellactin) intake of 1.75 grams will be safe and an acceptable daily intake of up to 9 grams orally could also be considered safe.

The composition and method may be administered under physician prescription or over the counter depending upon the formulation of the composition and the specific individual receiving treatment. In some embodiments the condition to be treated is The route of administration is in accord with known methods including without limitation; oral, sublingual, cutaneous, subcutaneous, mucosal, transmucosal, inhalation, intralesional, buccal, or by sustained release systems as noted below. In some embodiments the composition as herein provided is administered via a small strip or other form of material that may dissolve in the mouth of the patient. This allows the convenience of a solid form therapy while retaining the advantages of a sublingual or mucosal delivery. The enzymes of the human mouth are capable of dissolving carbohydrates but do not break down peptides or proteins or many types of organic molecule. Therefore the composition may be delivered directly to the bloodstream without being exposed to digestive enzymes or crossing the intestinal barrier, and without the necessity for intravenous delivery.

An effective amount of composition to be employed therapeutically will depend, for example, upon the specific composition, therapeutic objectives, the route of administration, and the weight and condition of the patient. Accordingly, the therapist may titer the dosage and modify the route of administration as required to obtain the optimal therapeutic effect. The clinician may administer the composition until a dosage is reached that achieves the desired effect. The progress of this therapy may be monitored by conventional assays or by the assays described herein.

The therapeutic composition can be administered through the skin, mucosa, nose, eye, or lung, in formulations including a liquid, cream, lotion, oil, emulsion, gel, paste, powder, liquid or powder aerosol (lyophilized). The composition may be administered parenterally or subcutaneously, intramuscularly, or intravenously as desired. The composition may be administered systemically, and may be sterile, pyrogen-free and in a parenterally acceptable solution having due regard for pH, isotonicity, and stability. These conditions are known to those skilled in the art. Briefly, dosage formulations of the compounds described herein are prepared for storage or administration by mixing the compound having the desired degree of purity with physiologically acceptable carriers, excipients, or stabilizers such as are non-toxic to the recipients at the dosages and concentrations employed.

Suitable examples of sustained-release preparations include semipermeable matrices of solid hydrophobic polymers containing the composition provided, which matrices are in the form of shaped articles, films or microcapsules. Examples of sustained-release matrices include polyesters, hydrogels (e.g., poly(2-hydroxyethyl-methacrylate), copolymers of L-glutamic acid and gamma ethyl-L-glutamate, non-degradable ethylene-vinyl acetate, degradable lactic acid-glycolic acid copolymers such as poly-D-(−)-3-hydroxybutyric acid.

The dosage of the composition herein for a given patient will be determined by the therapist or physician taking into consideration the natural molecule comprising the composition and various factors known to modify the action of drugs including severity and type of disease, body weight, sex, diet, time and route of administration, other medications and other relevant clinical factors. Therapeutically effective dosages may be determined by either in vitro or in vivo methods.

An effective amount of the composition herein to be employed therapeutically to increase cellular glutathione levels will depend, for example, upon the therapeutic objectives, the route of administration, and the condition of the patient. Accordingly, the therapist may titer the dosage and modify the route of administration as required to obtain the optimal therapeutic effect. A daily dosage might range from about 0.001 mg/kg to up to 100 mg/kg or more, depending on the factors mentioned above. The clinician may administer the therapeutic composition as provided herein until a dosage is reached that achieves the desired effect. The progress of this therapy may be monitored by conventional assays or as described herein.

It will be appreciated that administration of therapeutic entities in accordance with the compositions and methods herein may be administered with suitable carriers, excipients, and other agents that are incorporated into formulations to provide improved transfer, delivery, tolerance, and the like. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present composition, provided that the active ingredient in the formulation is not inactivated by the formulation and the formulation is physiologically compatible and tolerable with the route of administration and as known in the art.

The embodiments may be practiced in other specific forms. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

EXAMPLES

Example 1: Synthesis of Cellactin Procysteine

A multi-step organic synthesis of Cellactin consisted of classical oxazolidin and thiazolidin preparations by condensation of L-cysteine with a suitable reagent. The reaction mixture was quenched by temperature adjustment and pH control using HCl or NaOH as needed. Isolation used solvents to obtain first step of desired product. Final washing utilized an excess of purified water which was later removed by evaporation to yield highly purified Cellactin powder. Actual quality was confirmed by analytical procedures such as NMR and Optical Rotation parameters.

Reagents

Cysteine (52-90-4), Triphosgene (2315-10-9), Deionized water, Toluene (108-88-3), Sodium hydroxide (1310-73-2), Acetonitrile (75-05-8)

Protocol

Water was added to a container and cooled to 0° C.

Solid NaOH was added slowly.

The solution was then again cooled to 0° C.

Triphosgene was dissolved in toluene in a second container and mixed.

Cysteine was added to the 0° C. NaOH solution and again cooled to 0° C. Triphosgene solution was added slowly over a few hours to the Cysteine/NaOH solution so that the mixture was kept at 0° C. (±5° C.). The solution was stirred.

After all the Triphosgene solution was added, the solution was allowed to warm to 25-30° C.

The mixture was tested by NMR for % reaction completion. If not 100% reacted the solution was stirred until 100% reaction is completed.

Once 100% complete reaction the solution was pH adjusted to 1.5 with HCl or NaOH.

The mixture was concentrated and dried for 2 days at 60° C. under vacuum.

The dried powder was extracted with hot acetonitrile (70° C.) and filtered to remove insoluble material.

The acetonitrile layer was concentrated into a thick slurry.

The slurry was then filtered to afford a pale yellow solid that lightened considerably when rinsed with acetonitrile.

The solids were dried to remove traces of acetonitrile and further washed with water to purify to a >99.5% purity.

Cellactin has been evaluated in two Phase II clinical trials involving patients with ARDS. Treatment with Cellactin brand procysteine is a novel pharmacological approach to diseases associated with oxidative stress and resultant tissue damage such as ARDS and MOD. Procysteine provides a method for introducing the amino acid cysteine, an essential building block of glutathione, into cells. Preclinical studies have documented Procysteine's ability to increase intracellular levels of glutathione and prevent ROS damage.

Phase II trials with intravenously administered Procysteine have indicated the potential efficacy of procysteine in the treatment of patients with ARDS. In the first Phase II trial, which involved 32 patients treated with procysteine or placebo, procysteine-treated patients gained independence from mechanical ventilation a median of five days earlier than did placebo-treated patients. The second Phase II trial, which involved a total of 25 patients, indicated a similar reduction in median days on mechanical ventilation among procysteine-treated patients as compared with placebo-treated patients. Procysteine-treated patients also regained efficiency in transporting oxygen to the blood stream to a greater degree than did placebo-treated patients, as indicated by an established measure of lung function.

Based on procysteine's mechanism of action, the drug may have potential applications in other diseases. Additional phase I/II clinical trials with procysteine were conducted to determine its potential application for the treatment of amyotrophic lateral sclerosis and atherosclerotic cardiovascular disease.

Example 3: Evaluation of Potentially Toxic Processes

All raw materials used in the various synthesis steps were USP/FCC quality and quantified by molar calculations for complete reaction conversion. External chemical reaction variables such as optimum temperature and system pH, reaction time, and mixing condition criteria have been carefully determined to ensure quality parameters have been achieved. A critical reaction point was performed analytically by NMR to validate there is no unreacted L-cysteine material as required during cyclic conversion reaction. If NMR spectra indicated that any unreacted cysteine remains, additional mixing time was implemented followed by another test before continuing with remaining steps. Another critical point arose in the scheme to confirm that all added reaction solvent for product isolation and separation had been removed. NMR was again utilized to confirm the absence. If test result was positive, another rinse was made and followed by testing. If material passed, the entire batch was thoroughly dried and finished goods were subjected to product specification testing for validation.

Confirming the absence of triphosgene in the described Cellactin preparation process is crucial to the safety and use of the material. Testing points in manufacturing scheme were after solvent addition and water washing steps. The employed analytical test method is Spectrophotometric Fluorescence which is quantitative with detection limits of <0.4 micromol/L. Test requirement for Cellactin approval was the absence of any toxic substance.

Example 4: Historical Conditions of Use and Cumulative Exposure Estimate for the Historically Consumed Material In previous human clinical trials, procysteine, oral administration at 25-129 mg/kg (1.75-9 g/day), demonstrated significant increase in blood glutathione levels in a dose response manner. Across all clinical trials, only minor adverse experiences possibly related to procysteine treatment have been reported. In general, procysteine was well tolerated, including by a group of patients that orally consumed it at doses up to 9 grams per day for up to 2 years without clinically significant changes in serum chemistry or hematology. No statistical significant adverse events were observed in human clinical trials.

Example 5: Safety Study Type

The following tables are a compilation of known results and estimates of NOAEL/LOAEL for various animal species and humans. In most studies, no adverse effects were observed in the highest dose tested. In addition, genetic toxicity studies, Ames Test, Chromosome Aberration, and Mouse Micronucleus have been conducted and all of these studies were negative for genetic toxicity (i.e. non-genotoxic).

TABLE 1

| | | Preclinical Intravenous (IV) | | | | |
|---|---|---|---|---|---|---|
| Animal | Administration Method | NOAEL | LOAEL | Suggested human oral dose | Safety Margin Human Oral | Reference |
| Rat | Single IV | ≥2.4 g/kg[a] | — | 0.025 g/kg | 96× compared to IV rat | 1, 2 |
| Mouse | Single IV | ≥2.4 g/kg[a] | — | 0.025 g/kg | 96× compared to IV rat | 1, 2 |
| Dog | Single IV | ≥0.45 g/kg[a] | — | 0.025 g/kg | 18× compared to IV dog | 1, 2 |
| Rat, neonate | Once daily IV for 35 days | ≥0.45 g/kg[a] | — | NA[b] | NA[b] | 2, 3 |
| Rat | Once daily IV for 28 days | ≥2.4 g/kg[a] | — | 0.025 g/kg | 96× compared to IV rat | 2, 3 |
| Dog | Once daily IV for 28 days | ≥0.45 g/kg[a] | — | 0.025 g/kg | 18× compared to IV dog | 2, 3 |

[a]Highest dose tested
[b]NA = Not applicable in that not currently proposed for human neonates The results of over 100 published preclinical studies provide evidence that procysteine (Cellactin) is a safe and bioavailable source of cysteine effective in increasing glutathione levels. For example, supplementation of procysteine (Cellactin) in sulfur amino acid deficient rat diets preserved glutathione in rat lungs and leukocytes. Also, procysteine (Cellactin) treatment increased (repleted) tissue glutathione levels in acutely septic rats and rodent brains and maintained cellular glutathione levels when glutathione-depleting agents were administered to otherwise healthy animals. In fasted mice, procysteine (Cellactin) dietary supplementation increased liver glutathione levels.

TABLE 2

| | | Clinical Oral | | | |
|---|---|---|---|---|---|
| | Administration Method | NOAEL | Suggested human oral dose | Safety Margin Human Oral | Reference |
| Human HIV patients | Single IV followed 14 days later by six biweekly infusions for total of 13 administrations | ≥100 mg/kg/day[a] | 25 mg/kg/day | 4X compared to human IV | 2 |
| Human HIV patients | Single oral dose followed by 3000, 4500, 9000 mg/day for 28 days | ≥129 mg/kg/day[a] | 25 mg/kg/day | 5X compared to human oral | 2 |
| Human HIV patients | Oral daily for 6 months | ≥129 mg/kg/day[a] | 25 mg/kg/day | 5X compared to human oral | 2 |
| Human HIV patients | Oral ≥25 mg/kg daily for 1 week | ≥25 mg/kg/day[a] | 25 mg/kg/day | 1X compared to human oral | 11 |
| Human ARDS patients | IV 63 mg/kg every 8 hours for 10 days | ≥63 mg/kg/8 hours or 189 mg/kg/day[a] | 25 mg/kg/day | 8X compared to IV human | 2 |
| Human HIV patients | Orally up to 9000 mg/day for 2 years | ≥129 mg/kg/day[a] | 25 mg/kg/day | 5X compared to human oral | 2 |

[a] Highest dose tested

Example 6: Determination of the No-Observed-Adverse-Effect-Level (NOAEL) or Lowest-Observed Adverse Effect Level (LOAEL)

The following is a compilation of known results and estimates of NOAEL/LOAEL for various animal species and humans. In most studies, no adverse effects were observed in the highest dose tested.

TABLE 3

| | | Preclinical Intravenous (IV) | | | | |
|---|---|---|---|---|---|---|
| Animal | Administration Method | NOAEL | LOAEL | Suggested human oral dose | Safety Margin Human Oral | Reference |
| Rat | Single IV | ≥2.4 g/kg[a] | — | 0.025 g/kg | 96× compared to IV rat | 1, 2 |
| Mouse | Single IV | ≥2.4 g/kg[a] | — | 0.025 g/kg | 96× compared to IV rat | 1, 2 |
| Dog | Single IV | ≥0.45 g/kg[a] | — | 0.025 g/kg | 18× compared to IV dog | 1, 2 |
| Rat, neonate | Once daily IV for 35 days | ≥0.45 g/kg[a] | — | NA[b] | NA[b] | 2, 3 |
| Rat | Once daily IV for 28 days | ≥2.4 g/kg[a] | — | 0.025 g/kg | 96× compared to IV rat | 2, 3 |
| Dog | Once 28 days daily IV for for 28 days | ≥0.45 g/kg[a] | — | 0.025 g/kg | 18× compared to IV dog | 2, 3 |

[a] Highest dose tested
[b] NA = Not applicable in that not currently proposed for human neonates

TABLE 4

| | | Clinical Oral | | | |
|---|---|---|---|---|---|
| | Administration Method | NOAEL | Suggested human oral dose | Safety Margin Human Oral | Reference |
| Human HIV patients | Single IV followed 14 days later by six biweekly infusions for total of 13 administrations | ≥100 mg/kg/day[a] | 25 mg/kg/day | 4X compared to human IV | 2 |

TABLE 4-continued

Clinical Oral

| | Administration Method | NOAEL | Suggested human oral dose | Safety Margin Human Oral | Reference |
|---|---|---|---|---|---|
| Human HIV patients | Single oral dose followed by 3000, 4500, 9000 mg/day for 28 days | ≥129 mg/kg/day[a] | 25 mg/kg/day | 5× compared to human oral | 2 |
| Human HIV patients | Oral daily for 6 months | ≥129 mg/kg/day[a] | 25 mg/kg/day | 5× compared to human oral | 2 |
| Human HIV patients | Oral ≥25 mg/kg daily for 1 week | ≥25 mg/kg/day[a] | 25 mg/kg/day | 1× compared to human oral | 11 |
| Human ARDS patients | IV 63 mg/kg every 8 hours for 10 days | ≥63 mg/kg/8 hours or 189 mg/kg/day[a] | 25 mg/kg/day | 8× compared to IV human | 2 |
| Human HIV patients | Orally up to 9000 mg/day for 2 years | ≥129 mg/kg/day[a] | 25 mg/kg/day | 5× compared to human oral | 2 |

[a]Highest dose tested

Utilizing animal (dog and rat) data and comparing that to the recommended daily procysteine (Cellactin) intake of 1.75 grams or ~25 mg/kg, that represents 18× to 96× safety margin compared to acute NOAEL and repeat NOAEL intravenous administration in dogs (450 mg/kg) and rats (2400 mg/kg), respectively. It is reasonable to conclude that the safety margin would be even greater if compared to animal oral administration data.

Comparing the recommended oral, daily procysteine (Cellactin) intake of 1.75 g to that of the 9 grams per day taken for 2 years without clinically significant changes in serum chemistry or hematology, there would by a 5× safety margin, whereas it is possible that the safety margin when comparing to an adverse effect level would be considerably larger than 5×.

Example 7: Determination of the Acceptable Daily Intake (ADI)

Without knowing the NOAEL or LOAEL for humans and based on the report of 9 grams per day taken orally for 2 years without clinically significant changes in serum chemistry or hematology, an ADI of up to 9 grams per day should be considered acceptable.

Example 8: Determination of Estimated Daily Intake (EDI) and the EDI/ADI Ratio

Without knowing the NOAEL or LOAEL for humans and based on the report of 9 grams per day taken orally for 2 years without clinically significant changes in serum chemistry or hematology, the EDI and ADI both should be considered as <9 grams/day. This would then result in an EDI/ADI ratio of 9 grams/day/9 g/day=1.

Example 9: Determination of Margin of Safety

Without knowing the NOAEL or LOAEL for humans it is difficult to determine a true estimate of margin of safety. However, based on the report of 9 grams per day (129 mg/kg/day) taken orally for 2 years without clinically significant changes in serum chemistry or hematolog and comparing that to the recommended oral, daily Procysteine (Cellactin) intake of 1.75 grams (25 mg/kg/day) an estimate would result in 5×. However, it would be reasonable to assume that a much higher estimate of safety margin would be expected based on the 4-8× estimate comparing oral, daily Procysteine (Cellactin) intake of 1.75 grams to human intravenous NOAEL calculations shown above in section 4.1 and 18 or 96× comparing to dog and rat intravenous NOAEL calculations, respectively shown above in Section 4.1. It is reasonable to conclude that the safety margin would be even greater if compared to animal oral administration data.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method for making L-2-oxothiazolidine-4-carboxylate (procysteine), the method comprising:
    dissolving triphosgene in toluene
    reacting L-cysteine with the triphosgene dissolved in toluene in a reaction mixture;
    testing the reaction for completeness;
    continuing the reaction to completion if incomplete;
    cooling the reaction mixture to a temperature in a range of from about 0 degrees C. to about 20 degrees C.;
    concentrating and drying a product;
    isolating and washing the product;
    drying the product;
    testing the product for purity; and
    rewashing until the product reaches a purity in a range of from about 95 percent to about 100 percent.

2. The method of claim 1 further comprising dissolving L-cysteine in a solution of water and NaOH and mixing with the triphosgene dissolved in toluene.

3. The method of claim 2 further comprising adding a solution of triphosgene dissolved in toluene to the solution of water and NaOH slowly to form a two phase mixture while maintaining the temperature in a range of from about 0 degrees C. to about 30 degrees C.

4. The method of claim 3 further comprising allowing the two phase mixture to reach a temperature in a range of from about 15 degrees C. to about 55 degrees C. after the solution of triphosgene has been added.

5. The method of claim 4 wherein the temperature after the solution of triphosgene has been added is in a range of from about 25 degrees centigrade to about 30 degrees C.

6. The method of claim 4 further comprising adjusting the pH of the two phase mixture after the solution of triphosgene has been added to in a range of from about 1.0 to about 3.5 with HCl or NaOH.

7. The method of claim 6 wherein the pH is adjusted to 1.5.

8. The method of claim 1 wherein the purity is 99 percent.

* * * * *